United States Patent [19]

Gandhi et al.

[11] Patent Number: 4,461,184
[45] Date of Patent: Jul. 24, 1984

[54] COMPRESSED BREATHING AIR SAMPLING DEVICE

[75] Inventors: Shri K. Gandhi, Toronto; H. Dinsmore Madill, Brampton, both of Canada

[73] Assignee: Her Majesty the Queen in right of Canada, as represented by the Minister of National Defence, Ottowa, Canada

[21] Appl. No.: 396,189

[22] Filed: Jul. 8, 1982

[30] Foreign Application Priority Data

Jul. 10, 1981 [CA] Canada .................................. 381505

[51] Int. Cl.³ .............................................. G01N 1/22
[52] U.S. Cl. .............................. 73/863.23; 73/863.25; 73/863.31
[58] Field of Search ........... 73/863.25, 863.23, 863.21, 73/863.61, 863.31

[56] References Cited

U.S. PATENT DOCUMENTS

| 3,765,247 | 10/1973 | Riggs | 73/863.23 |
| 3,817,100 | 6/1974 | Anderson et al. | 73/863.23 X |
| 3,841,145 | 10/1974 | Boubel | 73/863.25 X |
| 3,965,748 | 6/1976 | Boubel et al. | 73/863.23 X |
| 4,014,216 | 3/1977 | Thornton et al. | 73/863.23 |
| 4,246,788 | 1/1981 | Olin et al. | 73/863.23 X |

FOREIGN PATENT DOCUMENTS 787938 12/1980 U.S.S.R. .......................... 73/863.23

OTHER PUBLICATIONS

"Flexible Bags Collect Gas Samples"; *Control Engineering*; 9-1967, F. J. Lourence et al.; p. 105.

*Primary Examiner*—S. Clement Swisher
*Assistant Examiner*—Tom Noland
*Attorney, Agent, or Firm*—Robert P. Gibson; Anthony T. Lane; Michael C. Sachs

[57] ABSTRACT

A compressed gas sampling device is shown which includes a pressure reducing orifice to permit collection of a gas sample at a low pressure. A filter cartridge is connected between a flow meter and a pressurized source for analysis and gas is passed through the cartridge for a predetermined period of time. The cartridge may then be analyzed by a laboratory to determine contaminants which may be present in the source gas under analysis.

16 Claims, 5 Drawing Figures

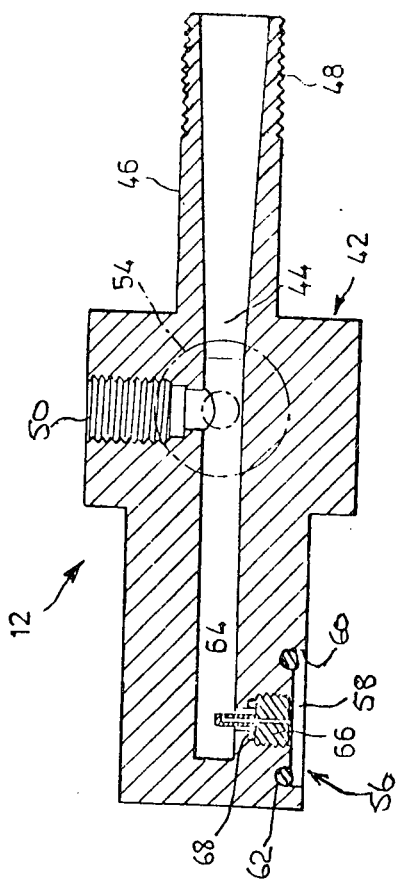
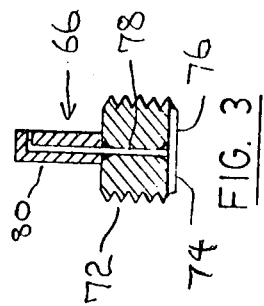
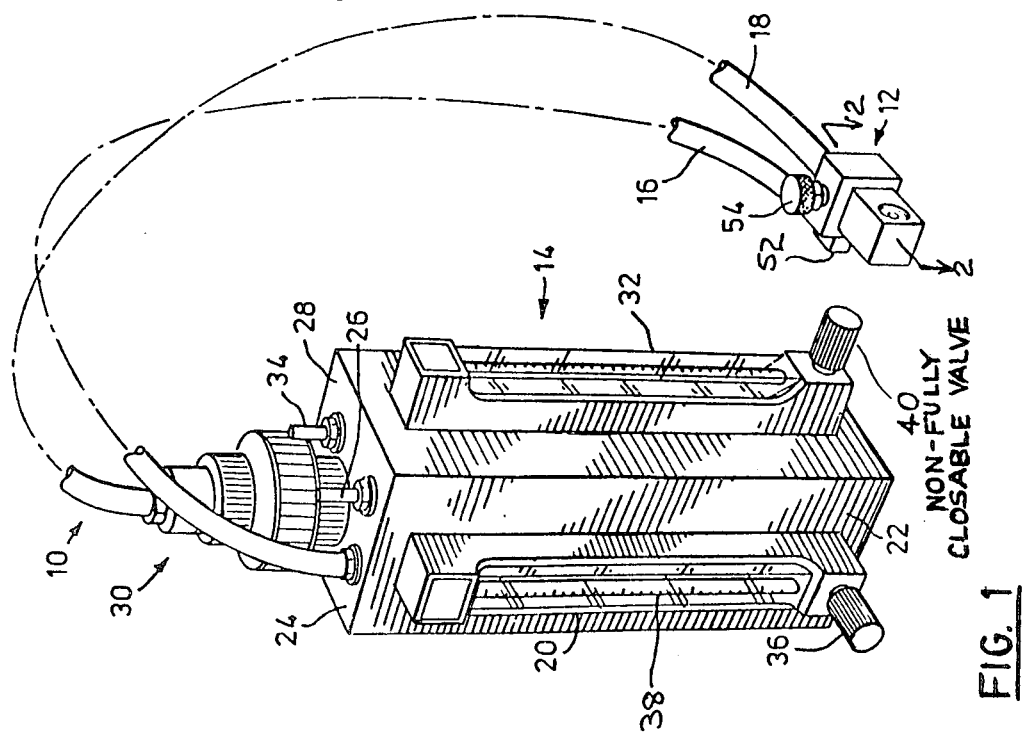

COMMERCIAL FILTER ASSEMBLY 4,461,184

COMPRESSED BREATHING AIR SAMPLING DEVICE

STATEMENT OF GOVERNMENT INTEREST

The U.S. Government has rights in this invention pursuant to Treaty, and may use the invention described herein without the payment of any royalties thereon or therefor.

BACKGROUND AND FIELD OF THE INVENTION

The present invention relates to apparatus for sampling a source of compressed gas and to a method of obtaining a sample of such gas.

Compressed gas is used in a wide range of environments as a convenient source of supply for breathing gas. There is therefore a requirement to analyze routinely the gas to ensure the purity of the gas and to ensure the safety of the user.

The purity of the compressed breathing gases in question may only be determined by laboratory analysis. This necessitates the collection of representative samples of the gas at the site of its use with subsequent shipment of the samples to a laboratory for comprehensive analysis. Such a comprehensive analysis is relatively complex requiring the services of a competent analytical laboratory, and there is difficulty in obtaining representative samples of the gas for the determination of contaminants such as oil mist, particulate matter and water.

The present techniques applied to breathing gases sampling and analysis require samples of the gas to be collected in pressure vessels which are then shipped to a central analytical laboratory for complete analysis of the contents.

This however presents a hazard associated with handling and shipping of high pressure gas samples and only provides a limited volume of sample for oil mist, water or trace aerosol contaminant detection. Further the accuracy of the results associated with analyzing the contents of a pressure vessel for oil mist or water are uncertain due to the tendency of these constituents to condense out on the wall of the pressurised sampling vessel and the initial cost and continuing maintenance by cleaning the pressure vessel makes the cost of this form of analysis high.

It is therefore an object of the present invention to obviate or mitigate the above disadvantages.

SUMMARY OF THE INVENTION

According to the present invention there is provided an apparatus for sampling a compressed gas source to identify contaminants therein said apparatus comprising a flow control member connectible to said source and a sample collecting means connected to said flow control member to receive gas therefrom, said flow control member including pressure reducing means to reduce the pressure of gas supplied to said sample collecting means.

In the preferred embodiment of the invention, the pressure reducing means includes the use of a series of interchangeable orifices which reduce the source pressure to an intrinsically safe low pressure.

LIST OF FIGURES

An embodiment of the present invention will now be described by way of example only with reference to the accompanying drawings in which:

FIG. 1 is a perspective elevation of a sampling apparatus,

FIG. 2 is a section on the line 2-2 of FIG. 1 showing a cross section of a flow control member.

FIG. 3 is an enlarged sectional view of an orifice used in the flow control member of FIG. 2.

DETAILED DESCRIPTION OF THE INVENTION

Figure 5:
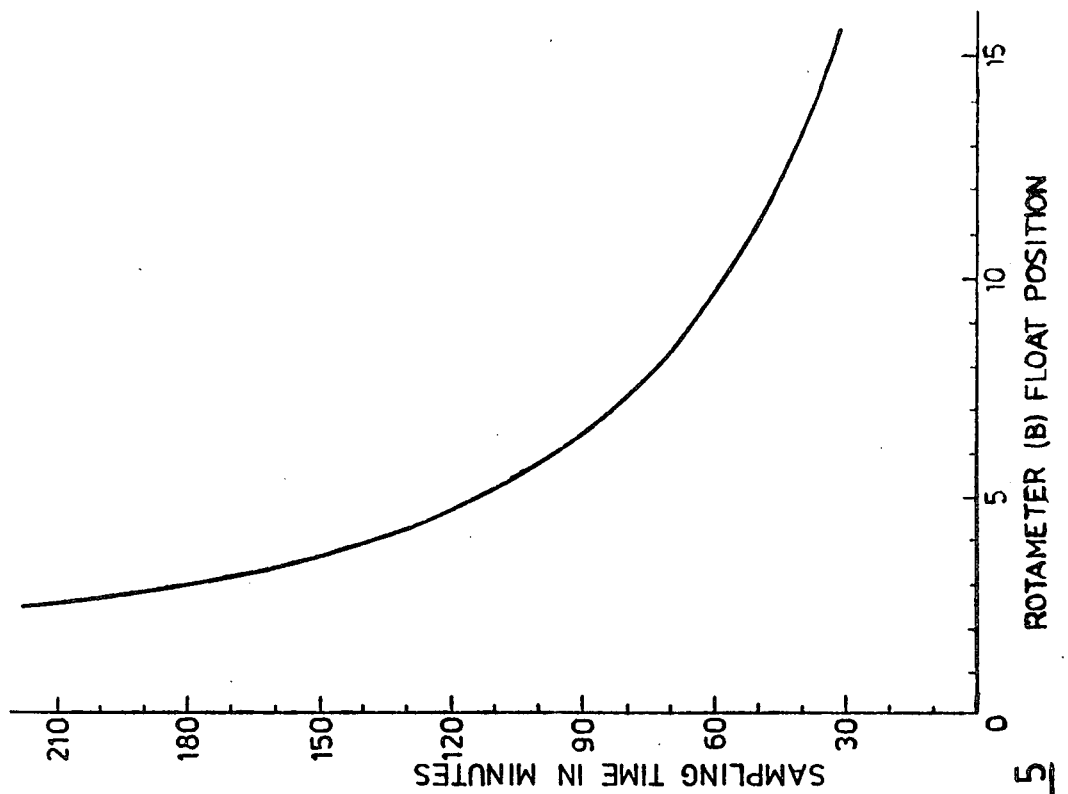
FIG. 5 is a curve indicating the relationship between the desired sampling time and the flow rate through the filter of FIG. 4.

Referring now to FIG. 1, a sampling apparatus 10 includes a flow control member 12 amd a sample collector 14. The flow control member 12 is connected to the sample collector 14 by a pair of tubes 16, 18. The tube 16 is connected to the inlet of a flow meter 20 mounted on a vertical wall 22 of a support plinth 24. The outlet to the flow meter terminates in a terminal member 26 mounted on the horizontal face 28 of the plinth 24.

The tube 18 is connected to a filter assembly 30 mounted on the horizontal face 28 and having an output connected to a flow meter 32. The outlet from the flowmeter 32 is vented to atmosphere through a conduit 34.

The flowmeter 20 includes a flow adjustment device 36 which controls the flow through the tube 16. The flow passing through the tube is indicated on a scale 38 mounted on the flow meter in known fashion.

Similarly the flow meter 32 includes a flow regulating device 40 which controls the flow through the tube 18. The flow regulating device 40 is arranged so that it cannot completely close the passage of gas through the tube 18 to prevent pressurization of the filter assembly 30.

The flow control member 12 is best seen in FIG. 2 and includes a body 42 with a longitudinal blind bore 44 extending from an outlet nozzle 46. The nozzle 46 is provided with a series of circumferential serrations 48 to assist in retaining the tube 18 which is connected to the nozzle 46 in location.

The bore 44 is intercepted by an outlet conduit 50 which is connected through an elbow 52 (FIG. 1) to the tube 16. The bore 44 is also intercepted by a pressure relief conduit (not shown) which connects to a safety relief valve 54 (FIG. 1) to prevent overpressurization of the tubes 16 and 18.

Admission of gas to the bore 44 is provided by an inlet nozzle generally designated 56. The nozzle includes a circular recess 58 which is relieved at its peripheral portion 60 to provide a seat for an O ring 62. The dimensions of the recess 58 are chosen to match the standard dimensions of a compressed gas filling yoke commonly associated with pressurized sources of compressed gas.

A central passage 64 connects the recess with the bore 44. The passage 64 is threaded to receive a jet 66 which seats against an O ring 68 provided on a shoulder of the passage 64. The jet 66 which is best seen in FIG. 3 includes a cylindrical body 72 having a thread formed on its periphery and a slot 74 cut into the end face 76 to receive a screwdriver blade. An orifice 78 is formed through the body 72 and is connected to an upstanding needle 80 projecting from the rear face 82 of the body. The needle 80 therefore projects into the bore 44 to provide restrictive connection between the bore and the recess 58.

The jets 66 are provided in sets with varying diameters of the orifice 78. A set that has found particularly utility in an embodiment of the apparatus is shown below.
1. 0.005" i.d.: Needle Gauge: No. 31
2. 0.007" i.d.: Needle Gauge: No. 29
3. 0.0095" i.d.: Needle Gauge: No. 26
4. 0.0155" i.d.: Needle Gauge: No. 22
5. 0.033" i.d.: Needle Gauge: No. 18

With these orifices, a wide range of source pressures can be accommodated whilst providing a controlled flow into the bore 44. The table below provides pressure range and flow range data obtained with the five jets dimensioned as set out above.

| Orifice Designation | Orifice Diameter (ins) | Pressure Range (PSI) | Flow Range (L/Min) |
| --- | --- | --- | --- |
| #1 | 0.005 | 1000–2500 | 4–25 |
| #2 | 0.007 | 500–1500 | 4–20 |
| #3 | 0.0095 | 180–600 | 4–20 |
| #4 | 0.0155 | 40–200 | 4–20 |
| #5 | | 0–50 | 0–25 |

Figure 4:
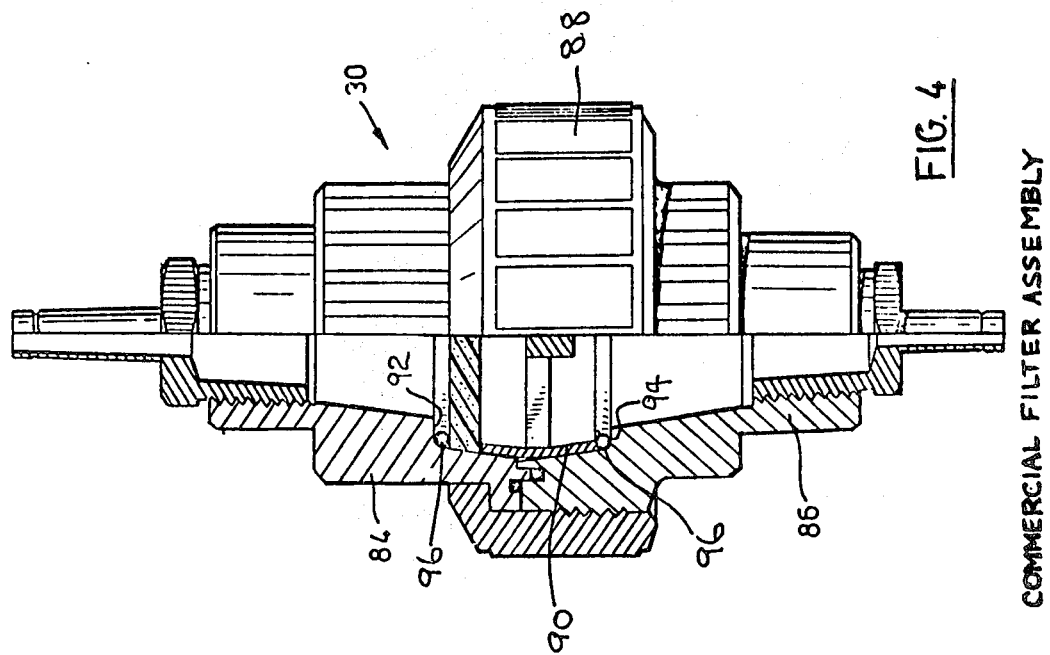
FIG. 4 is a part sectional view of a filter used in the apparatus of FIG. 1.

The filter assembly 30 is shown in FIG. 4 and includes a pair of separable casings 84, 86 which are held together by a threaded collar 88. A filter cassette 90 is held between a pair of opposed faces 92, 94 formed on the interior of the casings 84, 86 respectively. A pair of O rings 96 seal the cassette within the casing to ensure that all gas passing through the filter assembly 30 also passes through the filter cassette 90. The filter assembly is of known construction and is commercially available as a millipore AP14 microfibre-glass filter.

It will be seen therefore that upon mounting the body 42 to a gas filling yoke of the source to be sampled, gas will flow from the source through the orifice 78 and into the bore 44. Gas will pass along the tube 16 and flow meter 20 to the terminal member 26. Similarly gas will flow through the tube 18 and the filter assembly to the flow meter 32 from where it will be vented to atmosphere through conduit 34. During this flow, the contaminants in the gas will be collected by the filter cassette 90 which can subsequently be removed and forwarded to a laboratory for analysis and non-filtered samples of the gas can be collected from the terminal member 26. The apparatus 10 may be used in a number of different ways but one particular technique that has been successfully used to determine the contaminants in gas from a source will be described below.

Initially the pressure of the source is determined and a suitable jet 66 selected from the table shown above. The jet is then inserted into the body 42 with the O ring 68 located against the shoulder 70. The plinth 24 is then placed on a suitable horizontal surface so that the flow meters 20 and 32 are vertical. The valves 36 and 40 are fully opened so that maximum flow of gas can pass through the tubes 16, 18.

The filter assembly is then disassembled and a filter cassette 90 inserted with the filter side facing the inlet to the filter assembly. The body is then attached to the filling yoke of the source and gas will pass through the tubes 16, 18. The flow rate through the filter assembly as indicated on the scale of the flow meter 32 is used to determine the approximate sampling time required to ensure an adequate amount of particulate contaminance in the filter cassete 90. A typical graph is shown in FIG. 5 from which it will be seen that the sampling time can range from 30 to 210 minutes. The time during which gas is delivered to the flow meter 32 is noted and a uniform flow in the flow meter 32 is obtained by adjusting the flow control device 40 associated with the flow meter 32. The reading of the flow meter 32 is recorded on a data sheet which will subsequently be forwarded with the cassette to the laboratory.

After about five to ten minutes of continuous gas flow through the sampling apparatus 10, a gas tight bag is connected to the terminal member 26. The gas tight bag may be of any known type but a particular bag that has been used with some success are made from tedler p.v.f. film with a shut-off valve. The gas passing through the terminal member 26 is collected in the bag which is held lightly over the end of the terminal member to prevent overpressurization of the bag. After a sample has been collected, the shut-off valve of the bag is closed and the bag may then be forwarded to the laboratory together with the filter cassette 90.

To determine the water vapour present in the gas, colorimetric tubes may be used by connecting them to the terminal member 26. A particular colorimetric tube which has been used with success with the apparatus to detect water vapour is that made by Drager under order No. 6728531. The flow control device 36 on flow meter 20 is adjusted to provide the flow rates specified by the manufacturer of the colorimetric tube. This can be done at the same time as the filter sample flow provided the flow rate through the flow meter 32 remains constant. If, however, adjustment of the flow meter 20 to the desired rate causes a change in the flow to the flow meter 32, the water vapour determination should be taken after the completion of the filter sample. The gas from the terminal member 26 is passed until the specified volume of gas has passed through the colorimetric tube and the water vapour content noted from the markings on the tube. This is then recorded on a data sheet which will accompany the cassette and sample back to the laboratory. The volume of gas passing through the tube can readily be determined by noting the flow rate indicated by the flow meter 20 and calculating the time required to pass the specified volume of gas through the tube.

The terminal member 26 may also be used with other colorimetric tubes to determine other contaminants in a similar manner. For example, to determine the presence of carbon monoxide, a colorimetric tube sold by Drager under order Nos. 6728511 may be used. Similarly to determine the presence of carbon dioxide, a colorimetric tube sold by Drager under order No. 6728521 is used whereas colorimetric tube sold by Drager under order No. 6728371 may be used to sample the oil. In all cases, the flow control device 36 may be used to ensure that the flow rate through the terminal member 26 is that specified by the manufacturer of the tube.

Upon expiration of the time required for sampling through the filter assembly, the body member is removed from the filling yoke and the filter cassette removed from the casings. Blanking plugs are placed over the inlet and outlet to the cassette which is then dispatched with the gas tight bag and the data sheet in a mailing tube to the laboratory. The data sheet will note the total duration of the passage of gas through the filter, the flow rate of the gas and of course the readings obtained from using the colorimetric tubes.

In this manner, the laboratory has representative samples of the gas, and an indication of the contaminants in the gas as filtered out by the filter cassette 90 over an extended period. In addition, the apparatus is not pressurised and therefore the filter cassette and gas tight sampler can be handled without the need for pressure vessels.

While the invention may have been described with respect to a particular embodiment or embodiments, the invention also includes all modifications and substitutions within the spirit and scope of the invention, its description, or claims, as understood to those skilled in the art.

What is claimed is:

1. Apparatus for detecting presence and gathering samples of certain contaminants which may be present in a source of compressed gas to be analyzed, comprising:

flow control means for conveying gas from said source at selected rates of flow determined by selected needle shaped orifices placed within said flow control means, to a respective first and second tube means;

a unitary compact gas sample collection means comprising separate respective first and second gas sampling means, each fed respectively with gas by and only from the respective said first and second tube means;

said first gas sampling means comprising a first adjustable valve means for establishing a first rate of flow therein and a filter means for extracting certain contaminants from the gas flowing therethrough, in said first gas sampling means;

said second gas sampling means comprising a second adjustable valve means for establishing a second rate of flow therein, and an outlet terminal means for selective attachment of a gas bag means thereto for gathering over time a sample of the gas flowing in said second gas sampling means.

2. The apparatus as in claim 1 wherein said first gas sampling means further comprises a first measuring means for indicating the said first rate of flow, and said second gas sampling means further comprises a second measuring means for indicating the said second rate of flow.

3. The apparatus as in claim 2 wherein said first measuring means comprises a first flow meter, indexed with a readable scale, and said second measuring means comprises a second flow meter with an attached readable scale, for indicating flow rate.

4. The apparatus as in claim 2 further comprising optional colorimetric tube means for selective attachment to said outlet terminal for detecting certain contaminants which may be present in the second sampling means gas flow.

5. The apparatus as in claim 4 wherein the contaminant said colorimetric tube is selected for detecting is water vapor.

6. The apparatus as in claim 4 wherein the contaminant said colorimetric tube is selected for detecting is carbon monoxide.

7. The apparatus as in claim 4 wherein the contaminant said colorimetric tube is selected for detecting is carbon dioxide.

8. The apparatus as in claim 4 wherein the contaminant said colorimetric tube is selected for detecting is oil.

9. The apparatus as in claim 1 wherein said first gas sampling means has an open termination for allowing gas to escape to the atmosphere after passing through said filter means.

10. The apparatus as in claim 1 wherein the said first valve means is non-fully closable, to prevent stoppage of gas flow in said first sampling means which could overpressurize said filter means.

11. The apparatus as in claim 1 wherein said filter means comprises a filter assembly with a replacable filter which may be removed and sent for laboratory analysis of contaminants found thereon.

12. The apparatus as in claim 1 wherein said gas bag means comprises a gas tight tedler polyvinylflouride film bag having a shut-off valve thereon.

13. The apparatus as in claim 1 wherein the said flow control means further comprises a safety relief valve to prevent overpressurization of said first and second tube means.

14. The apparatus as in claim 13 wherein the said flow control means comprises nozzle features of standard dimensions for connection of said flow control means to standard scuba compressed gas equipment.

15. Apparatus for measuring contaminants which may be present in a source of compressed gas to be analyzed, comprising:

flow control means for conveying gas from said source at selected rates of flow determined by selected needle shaped orifices placed within said flow control means, to a respective first and second tube means;

a unitary compact gas sample collection means comprising separate respective first and second gas sampling path means, each fed respectively with gas by and only from the respective said first and second tube means;

said first gas sampling means comprising a first adjustable valve means for establishing a first rate of flow therein, a filter means for extracting certain contaminants from the gas flowing therethrough in said first gas sampling means; and a first measuring means for indicating the said rate of flow of gas in said first gas sampling means; said first valve means being non-fully closable to prevent overpressurization of said filter means;

said second gas sampling means comprising a second adjustable valve means for establishing a second rate of flow therein, a second measuring means for indicating the said second rate of flow of gas in said second gas sampling means, and an outlet terminal for selective attachment of a gas bag thereto for gathering over time a sample of the gas flowing in said second gas sampling means.

16. Apparatus for detecting certain substances which may be present in a source of compressed gas to be analyzed, comprising:

flow control means for conveying gas from said source at selected rates of flow to a respective first and second tube means;

a unitary gas sample collection means comprising separate respective first and second gas sampling means fed with gas by and only from the respective said first and second tube means;

said first gas sampling means comprising a first adjustable valve means for establishing a first rate of flow therein and a filter means for extracting certain substances from gas flowing therethrough; and said second gas sampling means comprising a second adjustable valve means for establishing a second rate of flow therein, and an outlet terminal means for selective attachment of a gas bag means thereto for gathering over time a sample of the gas flowing in said second gas sampling means.

* * * * *